US00PP08236P

United States Patent [19]

Spoto

[11] Patent Number: Plant 8,236

[45] Date of Patent: May 25, 1993

[54] ROSETTA ALMOND TREE

[76] Inventor: William Spoto, 760 N. Township Rd., Yuba City, Calif. 95991

[21] Appl. No.: 661,116

[22] Filed: Feb. 27, 1991

[51] Int. Cl.[5] ..... A01H 5/00

[52] U.S. Cl. ..... Plt./32.2

[58] Field of Search ..... Plt./30, 32.2

[56] References Cited

U.S. PATENT DOCUMENTS

P.P. 5,583 12/1985 Blickenstaff ..... Plt. 30

*Primary Examiner*—James R. Feyrer

*Attorney, Agent, or Firm*—Bernhard Kreten

[57] ABSTRACT

A new and novel almond tree which is particularly distinguished by a combination of desirable characteristics including attaining a large size at maturity, forming trees which can be trained to upright, relatively open, strongly branched, rounded shape, having medium amounts of healthy foliage, blooming substantially with and effectively pollenating "Nonpareil" and have comparable physical attributes and commercial value as the produce of the Nonpareil so the nut meats can be mixed therewith, and regularly producing, by about September 13, heavy crops of nuts of medium size, having cork characteristics which are nonpervasive to insects but which render kernels of large size desirable shape and good quality; and having nuts which are easily separated from hulls.

2 Drawing Sheets

DISCOVERY OF THE VARIETY

The present variety of almond was observed as a mature tree growing in an orchard acquired by the inventor which had been planted to various varieties of almonds. The orchard was purchased on Feb. 20, 1976. The orchard had been planted in the early 1900's. The original trees planted were on seedling almond rootstock. There were numerous seedling trees in the orchard. The orchard could have been planted from almond seeds or almond seedlings. The orchard did not produce in 1976 because the orchard had not been irrigated in 1975 and therefore the fruit buds did not develop. This orchard had been neglected for many years. Some of the seedlings in this orchard were bitter almond. Because of the many seedlings in this orchard, it was necessary to go through the entire orchard to be sure that there were no bitter almonds becuase they would cause degradation of the quality grade of the orchard. The tree of the present invention is an almond chance seedling. The parents of this new almond are unknown. As the almond of the present invention was observed, there were the qualities that many people have been looking for in a new variety. The inventor has been in the nursery business since 1958 and has been active as an orchardist his whole life and has the ability to identify almond cultivars. The orchard had been planted in a pattern of four rows of Nonpareil and four rows of Drake, but with numerous seedling almond trees present. The Drake and Nonpareil varieties can be clearly identified. The inventor observed the tree of the present invention growing uncharacteristically and took particular note of the distinctions between the present variety and the remainder of the inventor's orchard.

ASEXUAL REPRODUCTION OF THE VARIETY

A number of plants of the present variety of almond tree were asexually reproduced by budding; the work was done by the inventor who is a commercial nurseryman. At maturity, asexual reproductions of the instant almond tree variety produced fruit parts having the identical botanical and pomological characteristics as the parent. The almond is thought to be self incompatible, however, to date no specific self-pollination tests have been completed.

SUMMARY OF THE VARIETY

The present variety of almond trees are, characteristically, of large size, excellent vigor with an open, spreading, upright structure. Eventual tree height and density, however, is determined by pruning. Terminal growth vigor can be extremely variable, depending on modifying factors such as fertilization practices, frequency of irrigation, presence of soil nematodes, rootstock, soil type, etc. The tree is foliated in medium quantity, with large size, lanceolate abruptly pointed leaves having a finely serrate margin and globose glands; blooms early and heavily with pinkish white flowers; and is a consistent and medium to high yield productive bearer of a heavy, well set, crop of medium sized nuts having a well formed kernel of good quality.

The present variety of almond tree is further characterized in the following respects:

The claimed tree is of seedling source.

The petiole is of medium length and thickness in comparison with commercial almond cultivars currently grown in California. The tree develops an upright structure similar to the Neplus variety and is not as willowy as the Nonpareil.

The tree is an upright grower, with strong limbs. Very little limb damage has occurred despite heavy yearly production. The eventual density of the canopy and production of sucker sprouts is determined by pruning, because pruning methods and cultivation practices basically determine the tree size and shape.

The almond tree and nuts herein described may vary in slight detail due to climatic and soil conditions under which the variety may be grown; the present trees were grown in Sutter County (Yuba City, Calif.).

The tree blooms just prior to and concurrently with Nonpareil. The blossom is of average size and similar to that of Nonpareil and is an excellent pollenizer for Nonpareil thereby having utility for interplanting either in window or diamond type orchard plantings. As a pollenizer, the tree produces first-rate nuts that can be mixed with Nonpareil yielding no resultant decrease in value or grade.

The tree bears nuts which are loose in hulls and thus hull easily and are easily removed on harvest.

RESISTANCE TO INSECTS AND DISEASE

The nuts have a tighter cork than Nonpareil and are well sealed resulting in superior resistance to disease and insect pests in particular lepidopteran boring insects, such as the navel orange worm, *Amyelois transitella* (Walker) and the Peach twig borer, *Anarsia lineatella* (Zeller), two major pests of almonds which, in addition to physically damaging the crop, permit secondary infection by *Aspergillus flavus.* The suture of the shell has a lip more prominent than that of Nonpareil facilitating removal thereof.

BRIEF DESCRIPTION OF THE DRAWING

The drawings are an illustration, by photographic reproduction in color, depicting fruit of the variety; certain of such fruit being shown whole, while others are broken into halves with the fruit remaining in place in some of the related halves and while some of the fruit has been completely removed from the hull; and further depicting a mature almond tree as claimed herein.

DESCRIPTION OF THE VARIETY

The botanical details of this new and distinct variety of almond tree—with color definitions (except those in common color terms) referenced to Maerz and Paul Dictionary of Color (First Edition)—are as follows:

Tree:
- *Size.*—Large.
- *Density.*—Open.
- *Vigor.*—Excellent.

Trunk:
- *Size.*—Stocky.
- *Texture.*—Shaggy.

Branches:
- *Size.*—Stocky.
- *Texture.*—Medium.
- *Lenticels.*—Few. Large.
- *Branching habit.*—Upright.
- *Color.*—New wood — Brown, Dull. Mature wood — Brown. Dull.

Foliage:
- *Quantity.*—Medium.

Leaves:
- *Size.*—Medium. Average length — 100.3 mm. Average width — 20.9 mm.
- *Shape.*—Lanceolate. Abruptly pointed.
- *Thickness.*—Thin.
- *Texture.*—Smooth.
- *Margin.*—Finely serrate.
- *Petiole.*—Medium length. Medium thickness.
- *Glands.*—Average Number-2. Alternate. Small. Globose. Green Distal on petiole, and on blade.
- *Stipules.*—Wanting.
- *Color.*—Top side-Medium dark green (22-L-7). Under side-Dull lighter green (22-J-6).

Bloom:
- *Amount of bloom.*—Heavy.
- *Color.*—White.
- *Blooming period.*—February 26th–March 2nd. Comparable to Nonpareil.

Crop:
- *Bearing.*—Regular bearer.
- *Productivity.*—Heavy.
- *Distribution of nuts on tree.*—Well distributed.
- *Harvest period.*—September 10th–September 13th. Late, as compared to Nonpareil.
- *Tenacity.*—Hangs well on tree. Easy to harvest. Easy to hull.

Hull:
- *Outer surface.*—Rough.
- *Pits.*—Pitted.
- *Form.*—Regular.
- *Thickness.*—Thin.
- *Flesh.*—Tough.
- *Suture.*—Flat depressed.
- *Color.*—Light green (21-J-5) with silvery sheen.
- *Dehiscence.*—Opens freely.
- *Splitting.*—Along suture.

Nut:
- *Size.*—Medium. Average length — 37.6 mm. Average width — 21.4 mm. Average thickness — 14.8 mm. Average weight — 2.55 grams.
- *Form.*—Length/width — Elongated. Width/thickness — Medium.
- *Shell.*—Soft (i.e. easily cracked). Thin. Smooth. Outer shell — Hard (i.e. Non-porous, not easily fractured). Inner shell — Hard (i.e. well-sealed).
- *Color.*—Medium light brown (12-J-6).
- *Pits.*—Large. Few. Deep. Round.
- *Base.*—Ventrally oblique.
- *Stem scar.*—Large. Obtuse.
- *Apex.*—Obtuse. Sharp. Blunt. Tip recurved.
- *Wing.*—Narrow. Thin. Tapered toward base.
- *Inner surface.*—Dark colored.
- *Ventral streak.*—Dark. Narrow.
- *Percentage of kernel to nut.*—51%.

Kernel:
- *Size.*—(compared to Nonpareil). Large. Average length — 27.47 mm. Average width — 13.77 mm. Average thickness — 8.87 mm. Average weight — 0.55 gram.
- *Form.*—Length/width — Elongated. Width/thickness — Flat.
- *Base.*—Ventrally oblique.
- *Stem scar.*—Large. Obtuse.
- *Apex.*—Obtuse. Sharp. Shouldered. Tip recurved.
- *Texture.*—Wrinkled. Furrowed.
- *Pellicle.*—Thick.
- *Pubescence.*—Veined.
- *Color.*—Light brown (13-L-9).
- *Number of doubles.*—Low.
- *Flavor.*—Sweet.
- *Quality.*—Good.

I claim:

1. A new and distinct variety of almond tree is illustrated and described, particularly characterized by its upright tree form which is less willowy than Nonpareil; of large size; by blooming prior to and concurrently with Nonpareil and harvesting just after the Nonpareil; by excellent pollenization of other varieties such as Nonpareil; by bearing nuts that hull more easily and knock easily from the trees; by bearing nuts with a tighter, more well sealed cork imparting superior disease and insect resistance, the nuts being of superior quality and hulls easily, the nuts having meat which has comparable physical attributes and the same commercial value as the Nonpareil and can be mixed therewith at harvest.

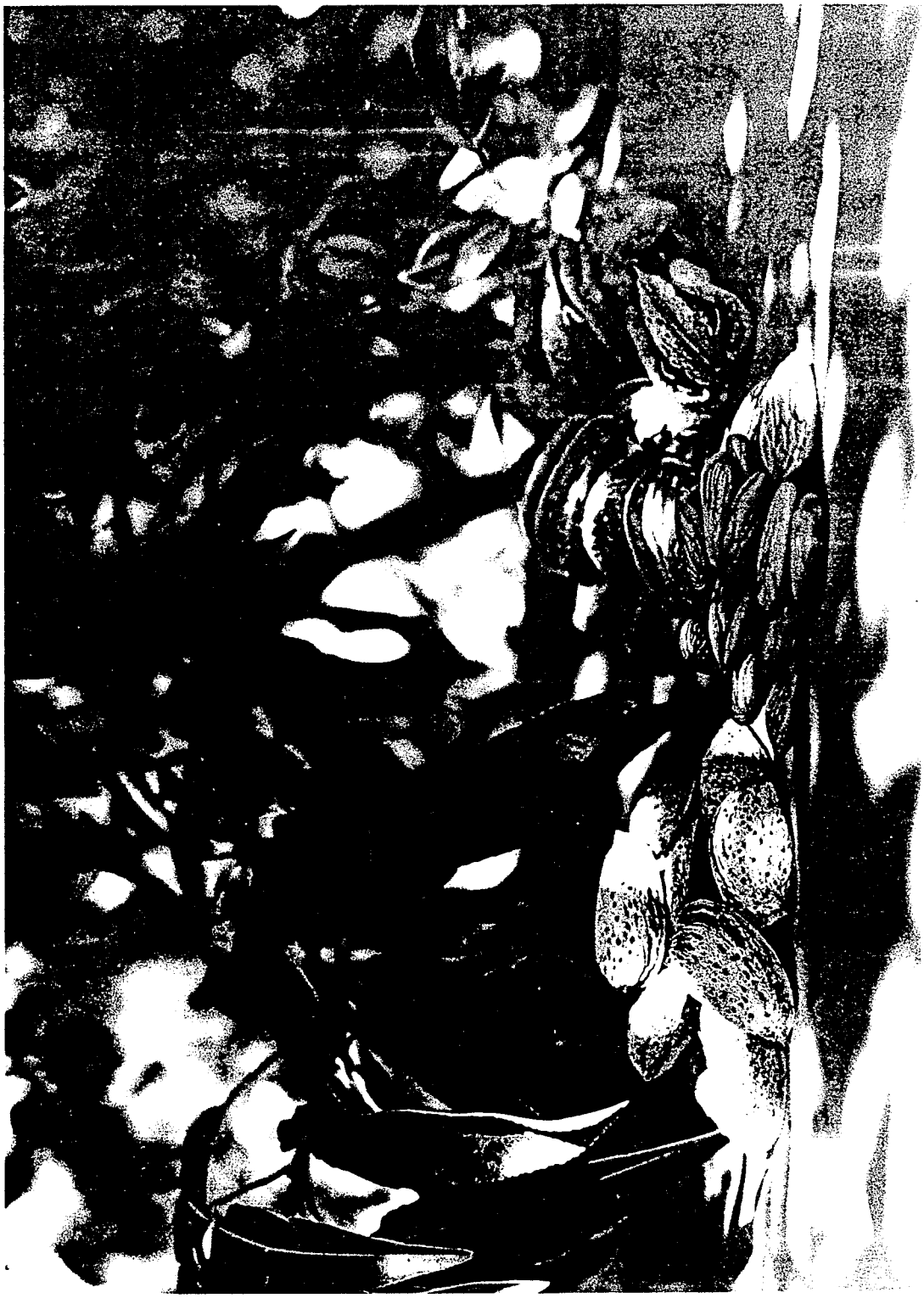

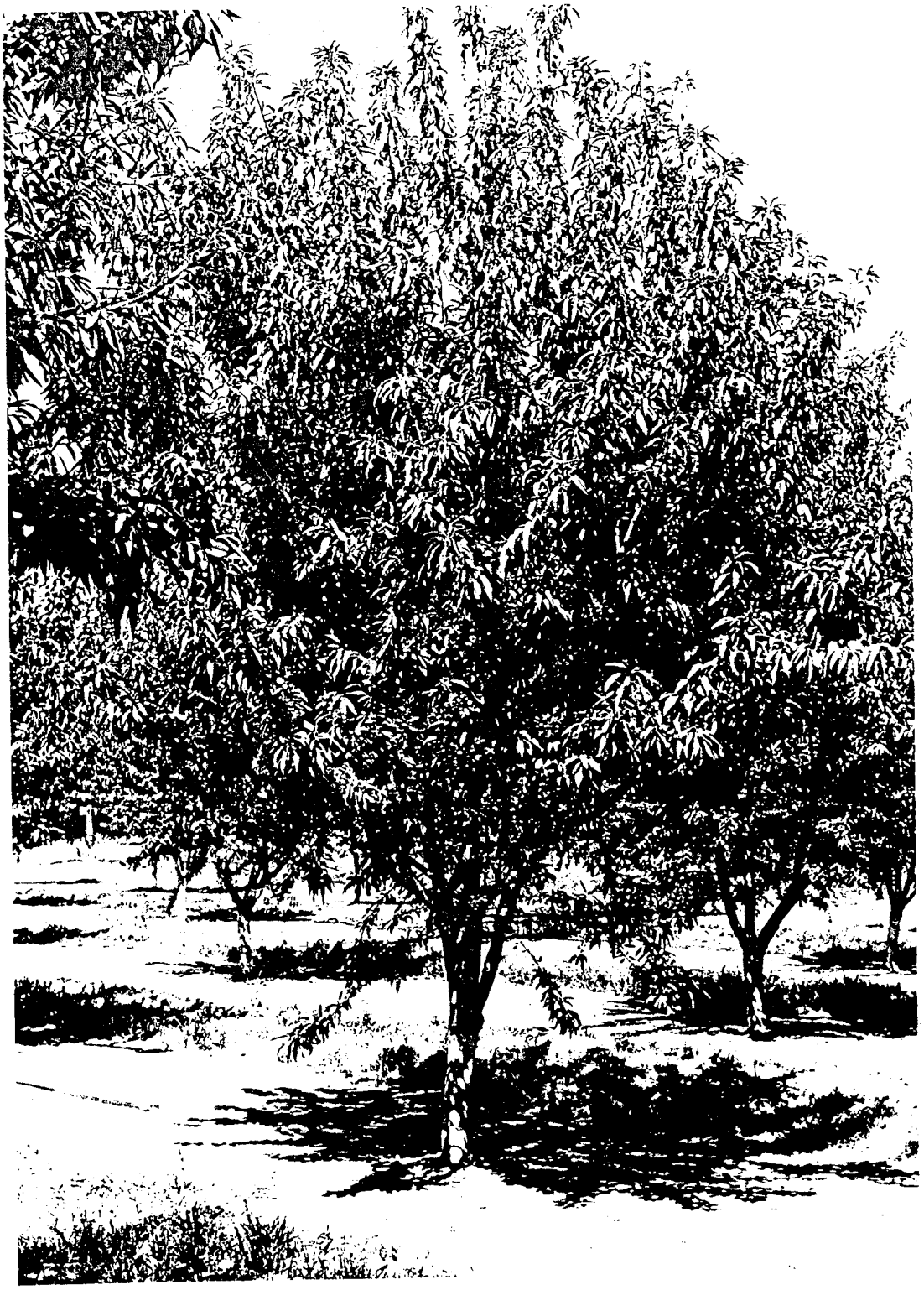

* * * * *